United States Patent [19]
Lin

[11] Patent Number: 6,071,242
[45] Date of Patent: Jun. 6, 2000

[54] METHOD AND APPARATUS FOR CROSS-SECTIONAL COLOR DOPPLER VOLUME FLOW MEASUREMENT

[75] Inventor: Gregory Sharat Lin, Fremont, Calif.

[73] Assignee: Diasonics Ultrasound, Inc., Santa Clara, Calif.

[21] Appl. No.: 09/107,704

[22] Filed: Jun. 30, 1998

[51] Int. Cl.$^7$ ............................................. A61B 8/06
[52] U.S. Cl. .............................................................. 600/456
[58] Field of Search .......................... 600/443, 454–456; 128/916

[56] References Cited

U.S. PATENT DOCUMENTS

| 4,257,278 | 3/1981 | Papadofrangakis et al. . | |
| 4,476,874 | 10/1984 | Taenzer et al. . | |
| 5,211,169 | 5/1993 | Freeland | 600/456 |
| 5,505,204 | 4/1996 | Picot et al. | 600/456 |
| 5,515,857 | 5/1996 | Tsujino et al. | 600/456 |
| 5,623,930 | 4/1997 | Wright et al. | 600/456 |
| 5,682,896 | 11/1997 | Scheib et al. . | |
| 5,769,079 | 6/1998 | Hossack . | |

Primary Examiner—Francis J. Jaworski
Attorney, Agent, or Firm—Blakely, Sokoloff, Taylor & Zafman

[57] ABSTRACT

A system is disclosed for measuring volume flow through vessel. A longitudinal area of a vessel in a body is scanned using a color Doppler imaging method, such that an imaging plane is formed approximately through the center of said vessel. A number of color pixels in a scanned cross-section of the vessel in which volume flow is detected are counted and tabulated. From this number of pixels, an observed cross-sectional area of the vessel is determined. Frequency shift information for each of the counted pixels is determined and these frequency shifts are spatially averaged. The instantaneous volume flow through the vessel is then computed from the cross-sectional area and frequency shift information. The volume flow for several different samples is computed. The instantaneous volume flows from each color Doppler imaging frame are temporally averaged over one or more integral cardiac cycles to compute a temporally-averaged volume flow.

22 Claims, 8 Drawing Sheets

METHOD AND APPARATUS FOR CROSS-SECTIONAL COLOR DOPPLER VOLUME FLOW MEASUREMENT

FIELD OF THE INVENTION

The present invention relates generally to medical devices, and more specifically to measuring volume flow through a vessel using an ultrasound method.

BACKGROUND OF THE INVENTION

Ultrasonic imaging technology has become a vital tool for examining the internal structure of living organisms. For the diagnosis of various medical conditions, ultrasonic imaging is often useful to examine soft tissues within the body to show the structural detail of internal tissues and fluid flow.

To examine internal body structures, ultrasonic images are formed by producing very short pulses of ultrasound using a transducer, sending the pulses through the body, and measuring the properties (e.g., amplitude and phase) of the echoes from tissues within the body. Focused ultrasound pulses, referred to as "ultrasound beams", are targeted to specific tissue regions of interest in the body. Typically, an ultrasound beam is focused at various steps within the body to improve resolution or image quality. Echoes are received by the transducer and processed to generate an image of the tissue or object in a region of interest. The resulting image is usually referred to as a B-scan image.

Measuring and imaging blood (and other bodily fluid) flow within a living subject is typically done using the Doppler principle, in which a transmitted burst of ultrasound at a specific frequency is reflected from moving blood cells, thereby changing the frequency of the reflected ultrasound in accordance with the velocity in the direction of the flow. The frequency shift (Doppler shift) of reflected signals with respect to the transmitted signals is proportional to the velocity of the fluid flow. This frequency may be detected and displayed on a video display device to provide graphic images of moving tissue structure and fluid flow within a living patient.

Present ultrasound techniques include single-plane or bi-plane duplex Doppler imaging of tissue motion, as well as cross-correlation ultrasound estimation of displacements and mean velocities for color mapping tissue motion (referred to as CVI and developed by Philips Corporation).

FIG. 1 is a diagram of a prior art single-plane duplex Doppler imaging method. In the single-plane duplex Doppler imaging method, a vessel 154 is scanned in the longitudinal plane by an ultrasound transducer 152 using duplex Doppler methods to manually measure vessel diameter, d. This method relies upon a range-gate value and a time-averaged angle-corrected mean velocity in the spectral Doppler waveform. The vessel diameter is then used to compute the cross-sectional area of the region-of-interest to determine the volume flow through the region.

Another present ultrasound technique for computing volume flow is bi-plane duplex Doppler imaging for vascular volume flow. In this method, a vessel is scanned in the transverse plane using B-scan techniques to manually measure the vessel cross-sectional area. The vessel is then scanned in the longitudinal plane with duplex Doppler to place the range-gate and to measure a time-averaged angle-corrected mean velocity in the spectral Doppler waveform. The volume flow is then computed using these values.

An alternative bi-plane duplex Doppler imaging technique is used for measuring cardiac output. For this method, a left ventricular outflow tract (LVOT) is scanned in the transverse plane with B-scan to manually measure cross-sectional area (ACS). The LVOT is then scanned in the longitudinal plane with duplex Doppler to place the range-gate and measure the velocity-time integral (VTI) and heart rate (HR). The cardiac output is then computed using the equation CO=VTI×ACS×HR. The cardiac output (CO) serves as a measure of volume flow.

In the Color Motion-mode (M-mode), non-Doppler correlation method (CVI-Q of Philips), color M-mode data is used to provide continuous sampling of vessel diameter. A non-Doppler correlation method is used to determine mean flow velocity. The vessel diameter is then used to compute cross-sectional area. The time-averages of cross-sectional area and mean velocity provide the data to compute the volume flow.

Although well established, these present known methods are generally subject to error because of simplifying assumptions about several factors regarding the vessel through which the fluid (typically, blood) is flowing. For example, roundness of the vessel, temporal invariance of the vessel cross-section, and velocity invariance throughout the vessel cross-section are often assumed. Such factors, however, may vary widely from one application to another. Other sources of error associated with one or more of the cited prior art methods include biased Doppler sampling in a frequency-domain spectrum, error in manual Doppler angle correction, or error in manual tracing of a vessel perimeter.

SUMMARY OF THE INVENTION

A system is described for measuring volume flow through a vessel using color Doppler ultrasound methods. A longitudinal area of a vessel in a body is scanned using a color Doppler imaging method, such that an imaging plane is formed approximately through the center of the vessel. A number of color pixels in a scanned cross-section of the vessel in which volume flow is detected are counted and tabulated. From this number of pixels, an observed cross-sectional area of the vessel is determined. Frequency shift information for each of the counted pixels is determined and these frequency shifts are spatially averaged. The instantaneous volume flow through the vessel is then computed from the cross-sectional area and frequency shift information using the relationship of volume flow being equal to the product of flow velocity and actual cross-sectional area. The volume flow for several different samples is computed. The instantaneous volume flows from each color Doppler imaging frame for these samples are temporally averaged over one or more integral cardiac cycles to compute a temporally-averaged volume flow.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which.

DETAILED DESCRIPTION

A system is described for measuring volume flow through a vessel sing color Doppler ultrasound methods.

It is an intended advantage of embodiments of the present invention to provide a device that measures volume flow through a vessel using color Doppler ultrasound methods without requiring Doppler angle correction.

It is a further intended advantage of embodiments of the present invention to provide a system that measures volume flow in real-time and that accurately accounts for the diameter or cross-sectional area of the vessel being scanned.

Various embodiments of the present invention may be implemented in discrete hardware components or, alternatively, in programmed processing units such as digital signal processors using software which is compiled, linked and then loaded from disk-based storage for execution during run-time. Various programs containing the methods employed in these embodiments may also reside in firmware or other similar non-volatile storage means.

Figure 2:
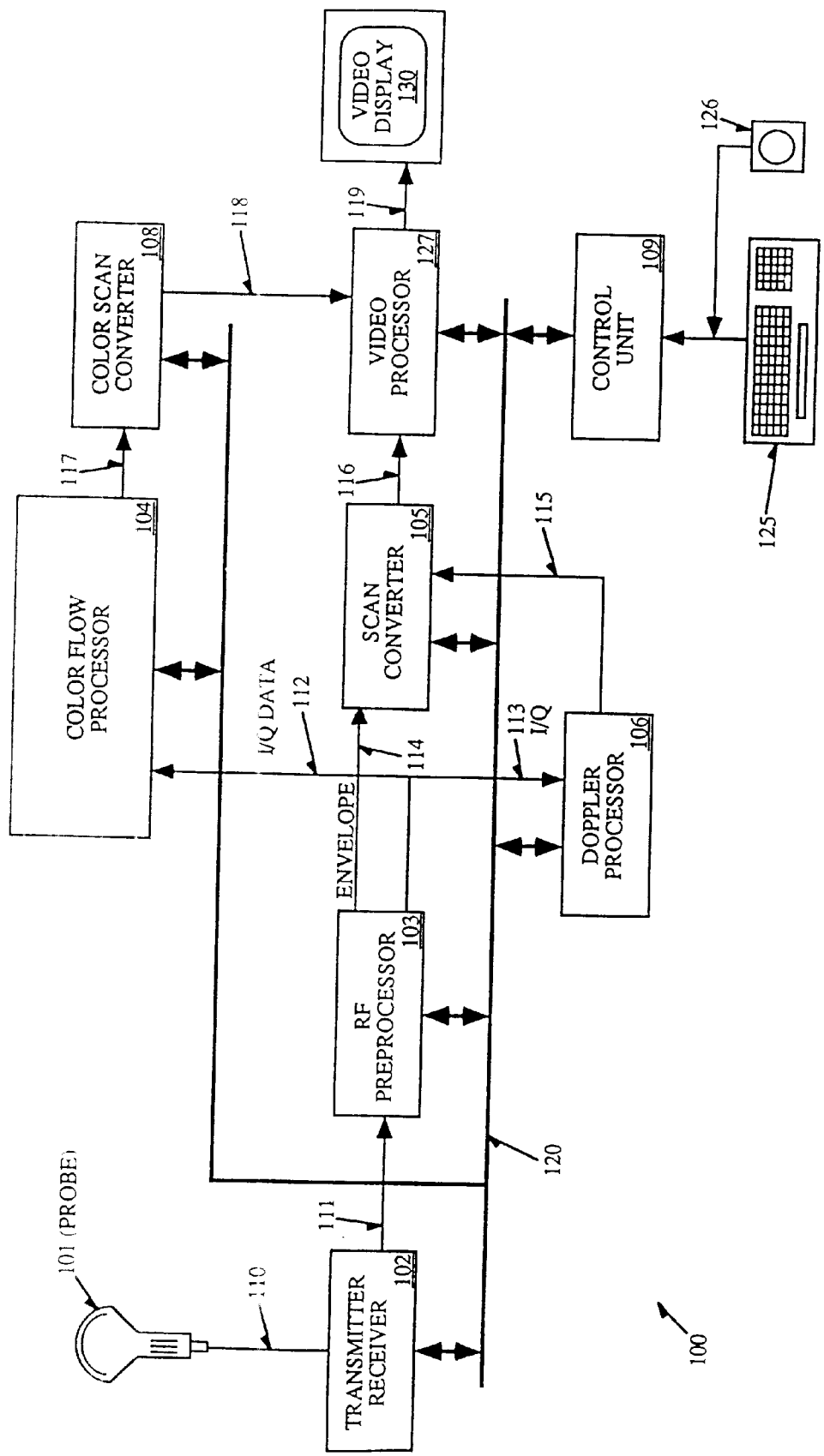
FIG. 2 is a block diagram of an ultrasonic imaging system that incorporates embodiments of the present invention.

FIG. 2 illustrates a block diagram of an ultrasonic imaging system that incorporates embodiments of the present invention. Imaging system 100 includes an ultrasonic transducer 101 (also referred to as a "probe"), which is typically a multi-element array of piezoelectric elements that both send and receive ultrasound signals when examining a subject, such as a living patient. Probe 101 is coupled through signal path 110 to transmitter/receiver circuit 102, which is designed according to principles known in the ultrasound imaging art, and which, for purposes of brevity, will not be discussed in further detail.

Transmitter/receiver circuit 102 is coupled to a control unit 109 through bus 120, and is controlled so that the elements in probe 101 are focused at particular points in the body during both transmission and reception of ultrasound signals. Transmitter/receiver circuit 102 and control unit 109 also often provide a scanning function so that a two-dimensional image may be generated without moving probe 101 with respect to the body.

Following transmission of ultrasound signals into the body, reflected signals are processed by a receiver (known as a "beamformer") in transmitter/receiver circuit 102. The multitude of signals from each individual element of probe 101 are converted into a single signal which is sent to radio frequency (RF) processor 103 through signal path 111. In one embodiment of the present invention, the beamformer circuit within transmitter/receiver 102 receives color Doppler pulses that provide sufficient frequency shift information to compute mean velocity and direction of flow of acoustic reflectors within the targeted area of the body.

RF processor 103 processes the signal information to produce a demodulated envelope signal and in-phase (I) and quadrature (Q) Doppler signals. The envelope signal represents the amplitude of echoes returning from the body and is further transmitted through signal path 114 to a scan converter 105. In one embodiment of the present invention, scan converter 105 is implemented as a large digital electronic memory.

Scan converter 105 stores the envelope echo information on a line-by-line basis together with the geometrical position of such information in the body resulting from the scanning process, in such a manner that a two-dimensional image may be constructed and transmitted to video processor 127 through signal path 116.

In the absence of any color Doppler information, video processor 127 simply sends an image signal over signal path 119 to video display monitor 130. This two-dimensional image, usually black and white, represents the distribution of echo generating sites within the body. The so-called B-scan image is then used by the operator to search the body for pathology or is used by a physician to develop a diagnosis.

I and Q signals for spectral Doppler are sent to Doppler processor 106 through signal path 113. Doppler processor 106, under the control of control unit 109 through bus 120, compares signals from several successive received echoes to determine the Doppler shift in a single region in the body which is commonly known as the sample volume. Doppler processor 106 also produces a continuous time series of spectral Doppler information in which blood flow velocities are displayed in black and white on video display 130 over one or more cardiac cycles (typically several seconds). The Doppler information is transmitted to scan converter 105 through signal path 115, and then to video processor 127 through signal path 116 for ultimate display on video display 130.

RF processor 103 transmits I and Q signals through signal path 112 to color flow processor 104. Color flow processor 104 typically processes several sample volumes along a given scanning direction in the body. Color flow processor 104 passes signals to color scan converter 108 through signal path 117. In color scan converter 108, color encoded signals are stored on a line-by-line basis, together with the geometrical position of such information in the body resulting from the scanning process. In this manner, a two-dimensional color video image is constructed and transmitted to video processor 127 through signal path 118.

Color scan converter 108, which may also be used to interpolate scan line information obtained from color flow processor 104, then transmits color Doppler information through signal path 118 to video processor 127 for display on video display 130. Video processor 127 typically includes decision circuits to choose whether a given specific part of the two dimensional image has color information resulting from flow or whether it only has echo information from static tissue. If flow is present, the color information is displayed at the correct point in the image rather than the black and white image information. In one embodiment of the present invention, color flow processor 104 processes instructions that allow system 100 to calculate and display velocity and direction information for tissue motion and fluid flow within the body.

Volume Flow Measurement

Figure 1:
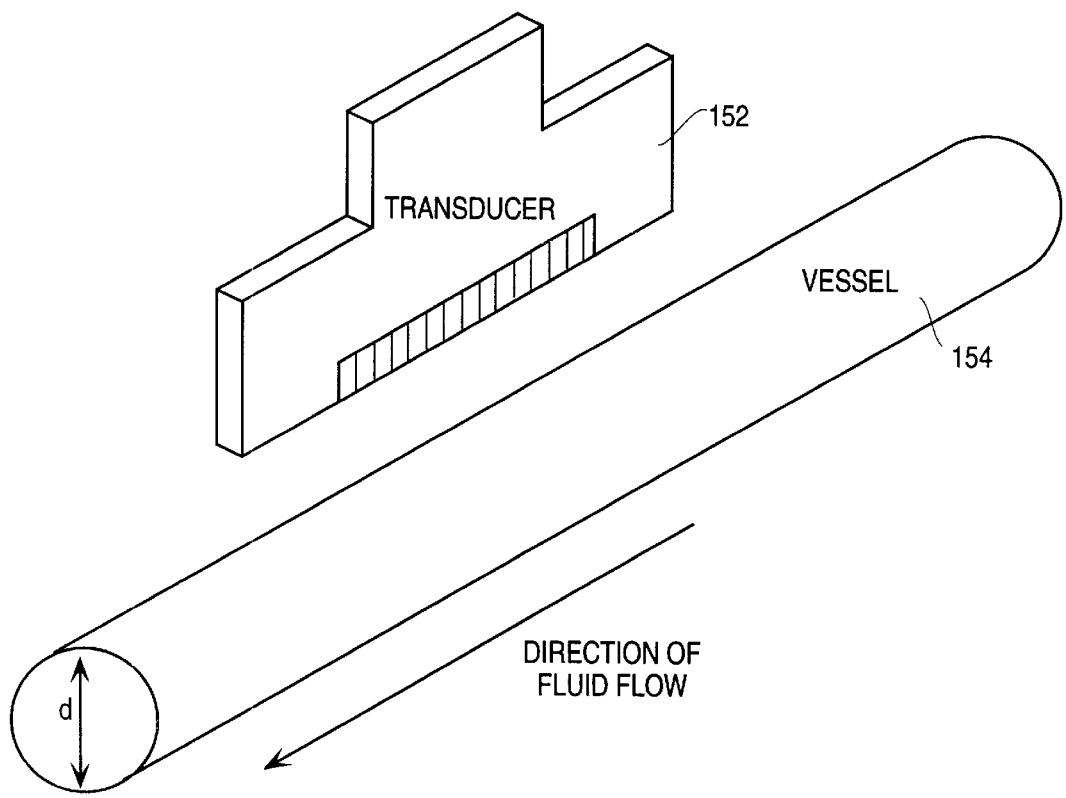
FIG. 1 is a diagram of a prior art single-plane duplex Doppler imaging method.

In one embodiment of the present invention, the ultrasound system of FIG. 1 incorporates a linear array ultrasound transducer and color Doppler ultrasound scanner that are used by an operator to measure the velocity and direction of acoustic reflector flow in vessels (e.g., blood vessels) in complex media. Processing circuits within ultrasound system 100 are configured to calculate volume flow using velocity and spectral frequency-shift information.

Two-Dimensional Imaging

In one embodiment of the present invention, volume flow through a fluid vessel (e.g., a blood vessel) in a body is computed by two-dimensional imaging and measurement of the cross-sectional diameter of the vessel. For this embodiment, a vessel in the region-of-interest is scanned in an imaging plane that follows a length of the vessel. The vessel is scanned using color Doppler imaging (CDI). The imaging plane is configured to cut longitudinally approximately through center of the vessel. The angle of Doppler interrogation is oriented such that a useful Doppler angle of less than or equal to 68 degrees relative to the direction of flow is provided.

Figure 3:
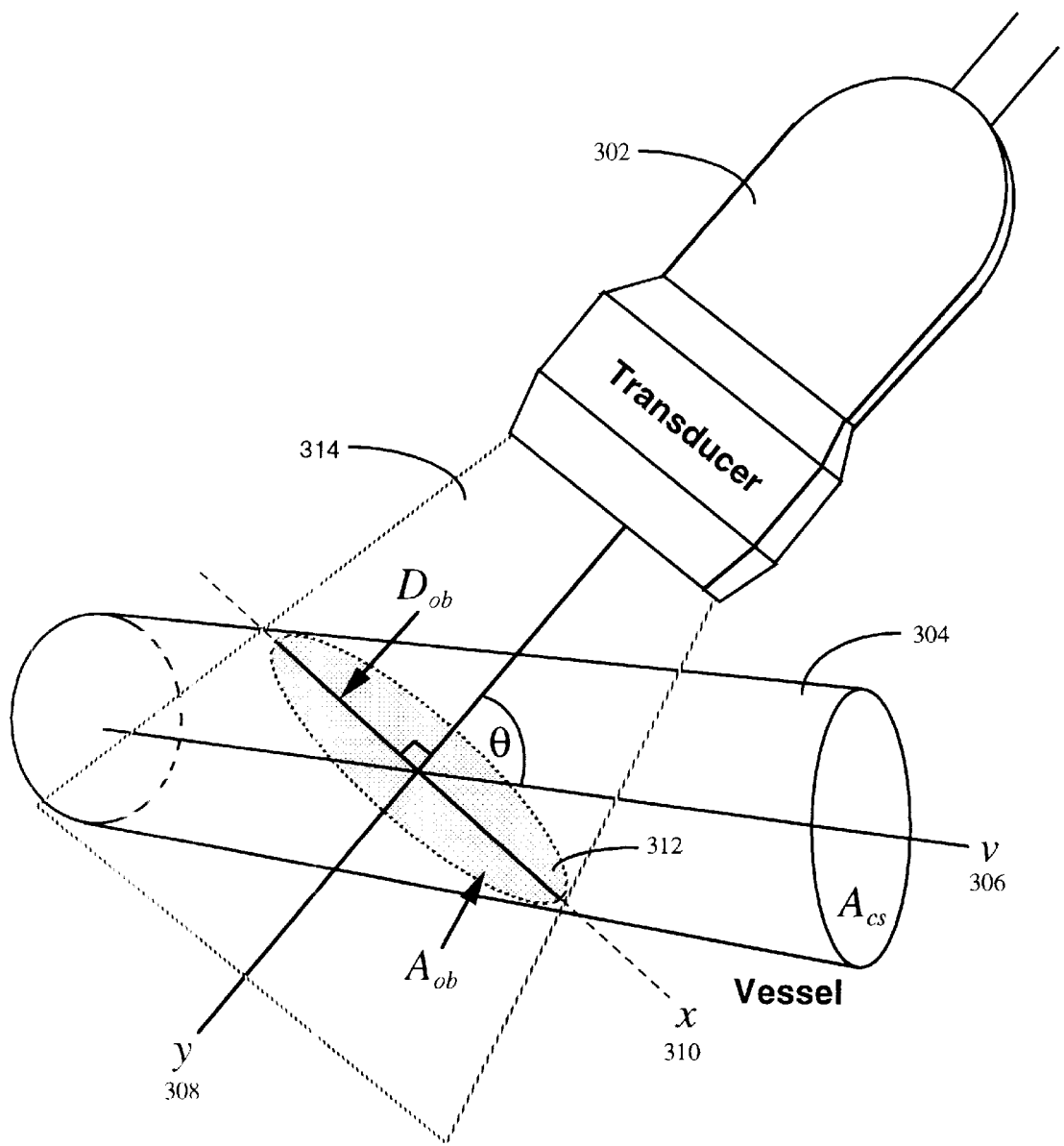
FIG. 3 illustrates the orientation of an ultrasound transducer relative to a vessel of interest for a two-dimensional imaging measurement technique, according to one embodiment of the present invention.

FIG. 3 illustrates the orientation of a transducer relative to a vessel of interest for a two-dimensional imaging measurement and technique according to one embodiment of the present invention. Vessel 304 of cross sectional area Acs contains a longitudinal axis that is designated axis v, 306. A linear array transducer 302 is oriented such that the linear array of ultrasound beams 314 is incident to the vessel along this longitudinal axis. The direction of ultrasound beams transmitted by transducer 302 is defined by a y-axis 308 extended from the center of the transmitting surface of transducer 302. The angle of incidence of the ultrasound beams is defined by the angle between y-axis 308 and the vessel axis, v, 306, and is denoted as angle $\theta$. For the color Doppler imaging system of one embodiment of the present invention, angle $\theta$ corresponds to the Doppler angle. For this embodiment, transducer 302 is positioned and oriented by the operator such that $\theta$ is less than or equal to 68° to provide a useful Doppler angle.

In vessel 304, an x-axis 310 is defined perpendicular to y-axis 308. The x-axis 310 goes through the entire cross-section of the vessel defined by area 312. In one embodiment of the present invention, the x-axis is used to define the axis of a cross sectional area of vessel v as defined by the angle of incidence of the ultrasound beams transmitted by transducer 302. As illustrated in FIG. 3, the area 312 of the vessel insonated by the ultrasound beams has an observed cross-sectional area denoted area $A_{ob}$. In one embodiment of the present invention, contiguous color pixels where flow is detected are tabulated to compute an observed cross-sectional diameter of vessel 304. This cross-sectional diameter is denoted $D_{ob}$.

Figure 4A:
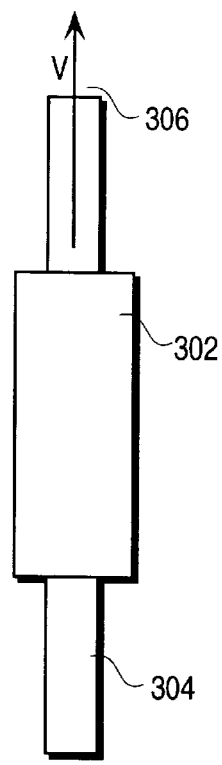
FIG. 4A illustrates a top view of the two-dimensional imaging technique illustrated in FIG. 3, according to one embodiment of the present invention.

FIG. 4A illustrates a top view of the two-dimensional imaging technique illustrated in FIG. 3, according to one embodiment of the present invention. Transducer 302 is shown as being oriented such that the ultrasound beams are incident along the length of vessel 304. Longitudinal axis 306 defines the direction of flow of fluid through vessel 304.

Figure 4B:
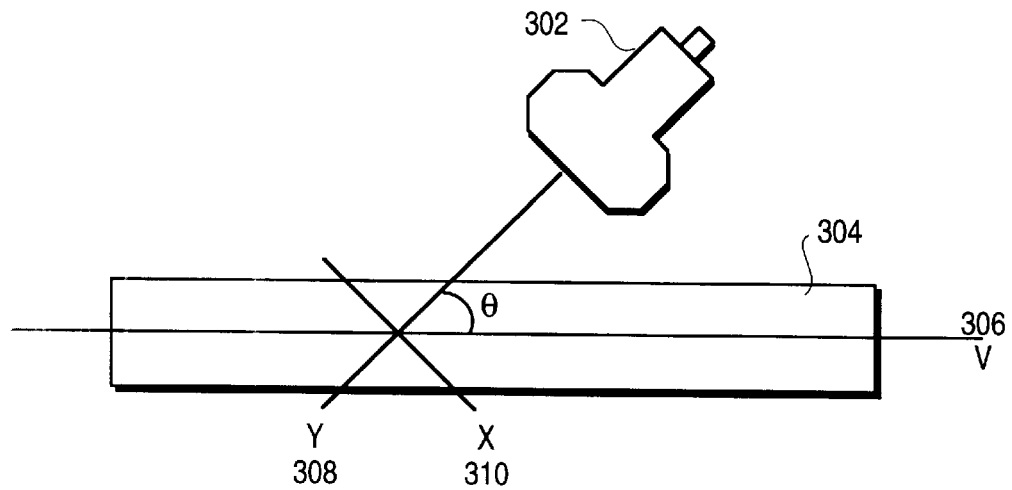
FIG. 4B illustrates a side view of the two-dimensional imaging technique illustrated in FIG. 3, according to one embodiment of the present invention.

FIG. 4B illustrates a side view of the two-dimensional imaging technique illustrated in FIG. 3, according to one embodiment of the present invention. Transducer 302 transmits ultrasound beams into vessel 304 along y-axis 308. Transducer 302 is angled relative to the longitudinal vessel axis 306 of vessel 304 by Doppler angle $\theta$. X-axis 310 perpendicular to y-axis 308 defines the observed diameter of vessel v for which fluid flow through the vessel is measured.

Three-Dimensional Imaging

In an alternative of the present invention, volume flow through a fluid vessel in a body is computed by a three-dimensional imaging and measurement of the cross-sectional diameter of the vessel. For this alternative embodiment, the vessel is scanned in an oblique cross-sectional imaging volume reconstructed from multiple parallel frames of color Doppler imaging (CDI). Each line of Doppler interrogation is oblique, and not perpendicular, in the y-axis (depth axis) relative to the direction of flow through the vessel in order to provide a useful Doppler angle of less than or equal to 68 degrees. For this embodiment, the transducer is oriented by the operator such that the x-axis (lateral axis) is approximately perpendicular to the direction of flow.

Figure 5:
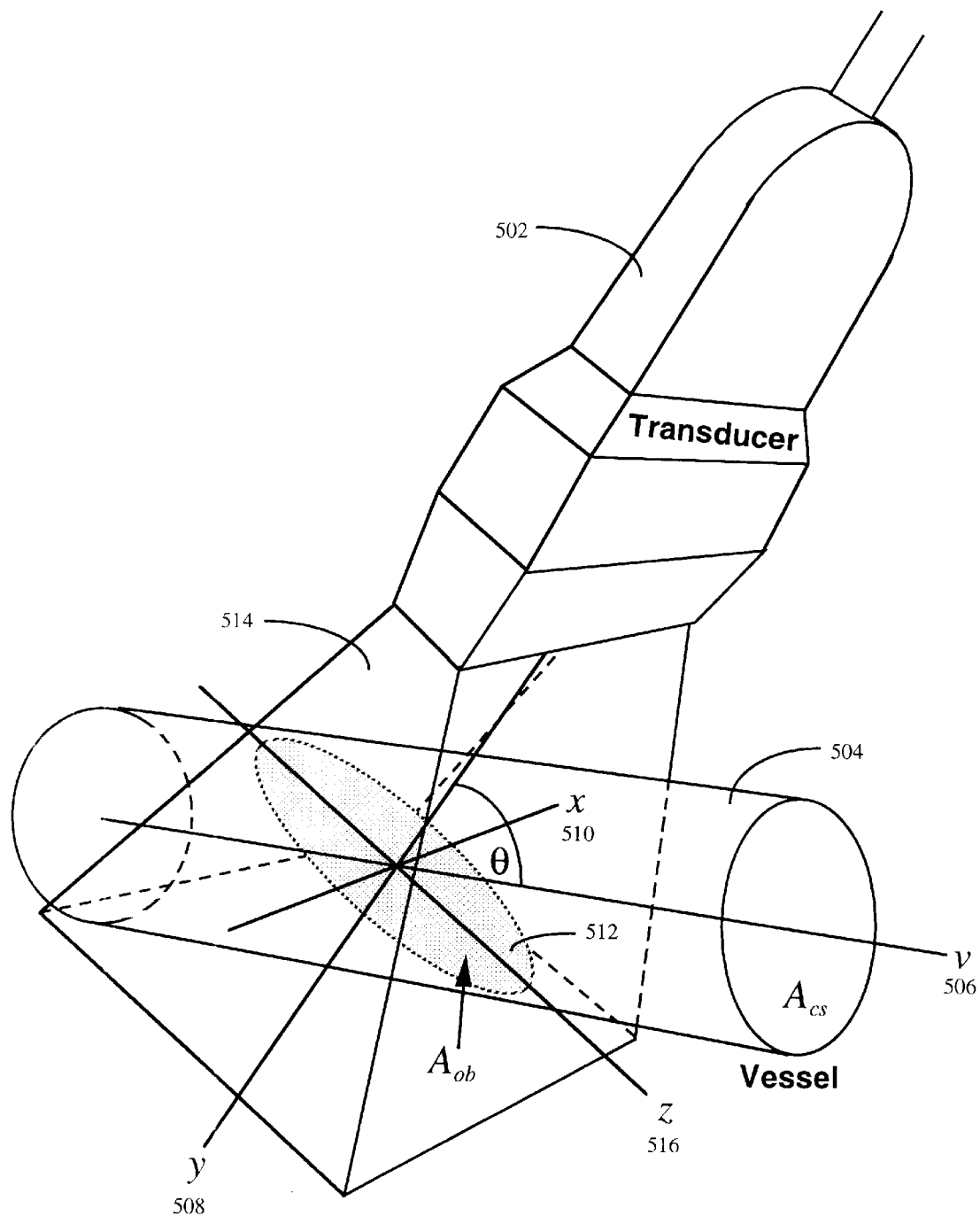
FIG. 5 illustrates the orientation of an ultrasound transducer relative to a vessel of interest for a three-dimensional imaging measurement technique, according to an alternative embodiment of the present invention.

FIG. 5 illustrates the orientation of an ultrasound transducer relative to a vessel of interest for a three-dimensional imaging measurement and technique according to this alternative embodiment of the present invention. A transverse plane is designated which goes through the entire cross-section of the vessel, and contiguous color pixels where flow is detected are tabulated to compute an observed cross-sectional area.

In FIG. 5, vessel 504 of cross sectional area $A_{cs}$ contains a longitudinal axis that is designated axis v, 506. A two-dimensional array or volume imaging transducer 502 is oriented by the operator such that the linear array of ultrasound beams 514 is incident to the vessel along a lateral axis that is approximately perpendicular to this longitudinal axis. The direction of ultrasound beams transmitted by transducer 502 is defined by a y-axis 508 extended from the center of the transmitting surface of transducer 502. The angle of incidence of the ultrasound beams is defined by the angle between y-axis 508 and the vessel axis, v, 506, and is denoted as angle $\theta$. For the color Doppler imaging system of one embodiment of the present invention, angle $\theta$ corresponds to the Doppler angle. For this embodiment, transducer 502 should be positioned and oriented by the operator such that $\theta$ is less than or equal to 68° to provide a useful Doppler angle.

In vessel 504, an x-axis 510 is defined that is parallel to the long axis of the face of transducer 502. As stated above, this x-axis should be approximately perpendicular to y-axis 508. The x-axis 310 goes through the entire cross-section of the vessel defined by area 512. In one embodiment of the present invention, the x-axis is used to define one axis of a cross sectional area of vessel 504 as defined by the angle of incidence of the ultrasound beams transmitted by transducer 502. In vessel 504, an oblique plane 512 that cuts through the entire cross-section of the vessel is defined by the x-axis and a z-axis 516. As illustrated in FIG. 5, this oblique plane 512 of the vessel insonated by the ultrasound beams has an observed cross-sectional area denoted area $A_{ob}$. The three-dimensional image of the cross-sectional area of vessel v is thus defined by the x, y, and z axes. In one embodiment of the present invention, contiguous color pixels where flow is detected are tabulated to compute an observed cross-sectional area of vessel 504. This cross-sectional area is denoted $A_{ob}$.

Figure 6A:
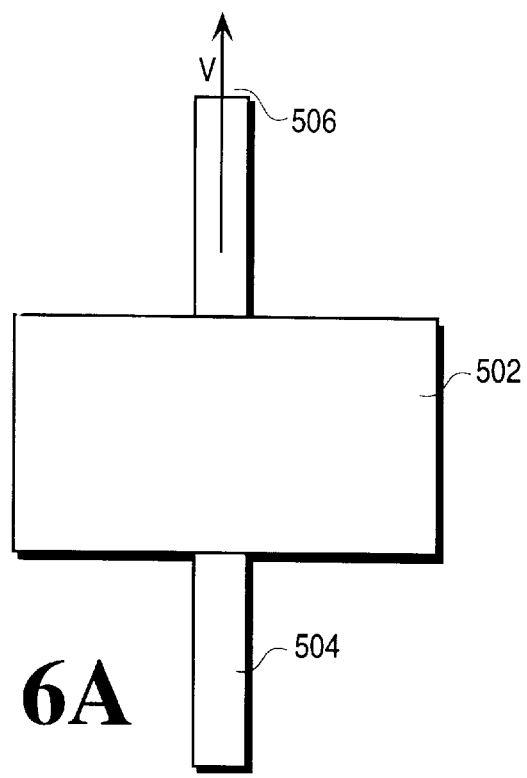
FIG. 6A illustrates a top view of the three-dimensional imaging technique illustrated in FIG. 5, according to an alternative embodiment of the present invention.

FIG. 6A illustrates a top view of the three-dimensional imaging technique illustrated in FIG. 5, according to the alternative embodiment of the present invention. Transducer 502 is shown as being oriented such that the ultrasound beams are incident across the direction of fluid flow 506 through vessel 504.

Figure 6B:
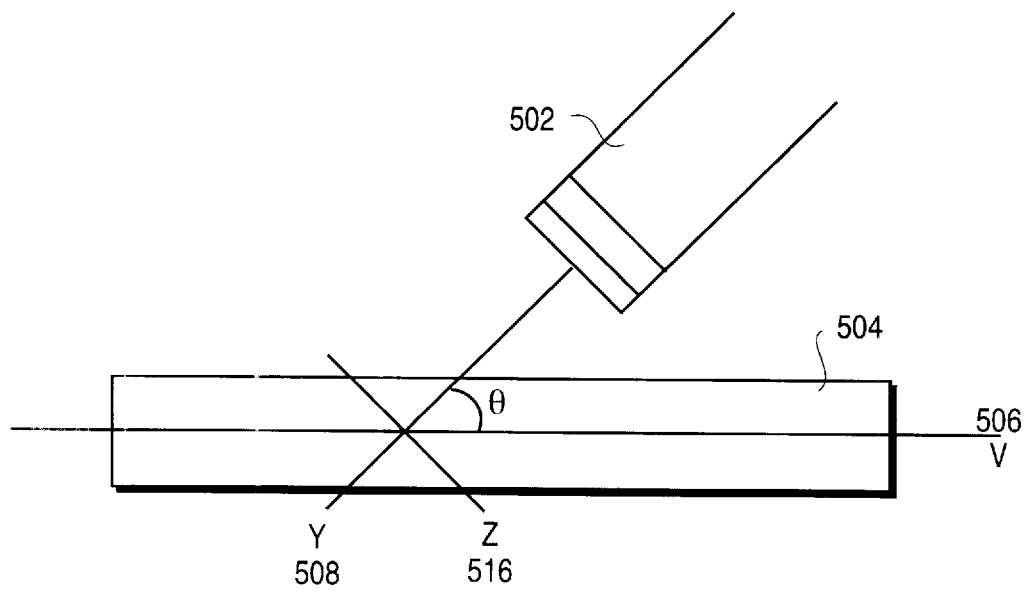
FIG. 6B illustrates a side view of the three-dimensional imaging technique illustrated in FIG. 5, according to an alternative embodiment of the present invention.

FIG. 6B illustrates a side view of the three-dimensional imaging technique illustrated in FIG. 5, according to the alternative embodiment of the present invention. Transducer 502 transmits ultrasound beams into vessel 504 along y-axis 508. Transducer 502 is angled relative to the longitudinal vessel axis 506 of vessel 504 by Doppler angle θ. The z-axis 516 perpendicular to y-axis 508 defines one observed diameter of vessel 504 for which fluid flow through the vessel is measured.

Volume Flow Computation

In one embodiment of the present invention, the cross-sectional area of the vessel of interest is determined using either the two-dimensional imaging technique illustrated in FIG. 3, or the three-dimensional imaging technique illustrated in FIG. 5. Once the vessel cross-sectional area has been determined by either method, the vessel cross-sectional area is continuously sampled by CDI filling of the vessel lumen, and counting all colorized pixels in the largest set of contiguous color pixels representing the same flow direction and temporally averaged over one or more cardiac cycles. In one embodiment of the present invention, a color Doppler imaging (CDI) technique that inherently provides mean-frequency shifts is used. These frequency shifts are spatially averaged over all pixels in the vessel lumen and temporally averaged over one or more cardiac cycles. Volume flow is then computed from a temporally-averaged value of observed vessel cross-sectional area $\overline{A\text{+sc ob}}$ and a spatial-mean/mean-frequency shift $\overline{\Delta f}$.

In one embodiment of the present invention, the instantaneous volume flow through the vessel is computed from the cross-sectional area and frequency shift information using the relationship of volume flow being equal to the product of flow velocity and cross-sectional area. The volume flow for several different samples is computed. For a number of different samples, the volume flow, $F_{v_i}$, for each ith sample is calculated using the following relationship:

$$F_{v_i} = \frac{\overline{\Delta f_i}}{2 f_{tx}} \cdot c \cdot A_{ob_i} \quad [1]$$

In equation [1], $\Delta f$ is the mean frequency shift, c is the velocity of sound in soft tissue, $f_{tx}$ is the Doppler transmit frequency, and $A_{ob}$ is the observed cross sectional area of the vessel.

The instantaneous volume flows from each color Doppler imaging frame for these samples are temporally averaged over one or more integral cardiac cycles to compute a temporally-averaged volume flow. The instantaneous volume flows for the samples are temporally averaged using the following relationship:

$$\overline{F}_v = \sum_i^n \frac{F_{v_i}}{n} \quad [2]$$

In equation [2], n is the number of samples for which instantaneous volume flows are calculated.

The velocity v obtained by Doppler means at a given sample volume is computed by the following equation:

$$v = \frac{\Delta f \cdot c}{2 f_{tx} \cdot \cos\theta} \quad [3]$$

In equation [3], $\Delta f$ is the mean frequency shift, c is the velocity of sound in soft tissue, $f_{tx}$ is the Doppler transmit frequency, and θ is the Doppler angle.

The calculation of the actual cross-sectional area depends on the angle of incidence of the ultrasound pulses transmitted by the ultrasound transducer into the vessel of interest. The ultrasound transducer is positioned at an angle θ (Doppler angle) relative to the vessel, and thus produces an image along an oblique plane through the vessel with an observed cross-sectional area that is a distorted version of the actual cross-sectional area. The actual cross-sectional area is calculated by multiplying the observed cross-sectional area by the cosine of the Doppler angle, θ.

In one embodiment of the present invention, the actual cross-sectional area $A_{cs}$ of the vessel is given by the equation, $A_{cs}=(\pi/4)D_{ob}^2 \cos\theta$. For this equation, $D_{ob}$ is the observed oblique cross-sectional diameter from which the observed cross-sectional area, $A_{ob}$, is estimated based on an assumption that the vessel cross-section is circular. This embodiment corresponds to the two-dimensional imaging technique illustrated in FIG. 3.

The volume flow through the vessel of interest can be calculated using the observed oblique cross-sectional diameter, $D_{ob}$, using the two-dimensional imaging method. The volume flow is denoted $F_v$, and is calculated using the following equation:

$$F_v = \overline{v} \cdot \overline{A_{cs}} \quad [4]$$
$$= \frac{\overline{\Delta f} \cdot c}{2 f_{tx} \cdot \cos\theta} \cdot \overline{A_{ob}} \cdot \cos\theta$$
$$= \frac{\overline{\Delta f}}{2 f_{tx}} \cdot c \cdot \frac{\pi}{4} D_{ob}^2$$

It should be noted that both the velocity and the observed cross-sectional area are dependent on the oblique Doppler angle. However, it should be noted that the angle-dependent terms (i.e., cos θ) cancel out in the computation of volume flow. This cancellation yields an angle-independent measurement, subject only to the limitation that θ≦68°.

In an alternative embodiment of the present invention, the actual cross-sectional area $A_{cs}$ of the vessel is given by the equation, $A_{cs=Aob} \cos\theta$. For this equation, $A_{ob}$ is the observed oblique cross-sectional area. This alternative embodiment corresponds to the three-dimensional imaging technique illustrated in FIG. 5.

The volume flow through the vessel of interest can be calculated using the actual cross-sectional area, $A_{cs}$ using either the three-dimensional imaging method. The volume flow is denoted $F_v$, and is calculated using the following equation:

$$F_v = \overline{v} \cdot \overline{A_{cs}} \quad [5]$$
$$= \frac{\overline{\Delta f} \cdot c}{2 f_{tx} \cdot \cos\theta} \cdot \overline{A_{ob}} \cdot \cos\theta$$
$$= \frac{\overline{\Delta f}}{2 f_{tx}} \cdot c \cdot \overline{A_{ob}}$$

In the above equations, $\overline{\Delta f}$ and $\overline{A\text{+sc ob}}$ are temporally averaged over one or more complete cardiac cycles.

It should be noted that both the velocity and the observed cross-sectional area are dependent on the oblique Doppler angle. However, it should be noted that the angle-dependent terms (i.e., cos θ) cancel out in the computation of volume flow. This cancellation yields an angle-independent measurement, subject only to the limitation that θ≦68°.

The above equations enable measurement of volume flow through a vessel in conjunction with color Doppler imaging techniques to track vessel cross-sectional area continuously in real-time. The velocity of fluid flow is tracked over time at each individual color pixel in the observed cross-sectional diameter, or cross-sectional area. The cross-sectional area is calculated by direct measurement in the three-dimensional method illustrated in FIG. 5. Using the two-dimensional method illustrated in FIG. 3, the cross-sectional area is derived indirectly by estimation from the oblique vessel diameter. In one embodiment of the present invention, the calculations required to determine the vessel cross-sectional area are performed in a processor, such as control unit 109 in FIG. 2, in an ultrasound imaging system, such as system 100 in FIG. 2. The calculated cross-sectional areas and fluid flow values are then processed in a video processor for display on a display device, such as video display 130 in FIG. 2.

Embodiments of the present invention described above provide several advantages over present methods of volume flow measurement.

The vessel cross-sectional area is tracked continuously in real-time, and the velocity of fluid flow is tracked at each individual color pixel in the cross-sectional area over time. The spatial velocity distribution is automatically accounted for by tracking each color pixel. Velocity information is read out at each individual point within a vessel directly without requiring Doppler angle correction.

Figure 7:
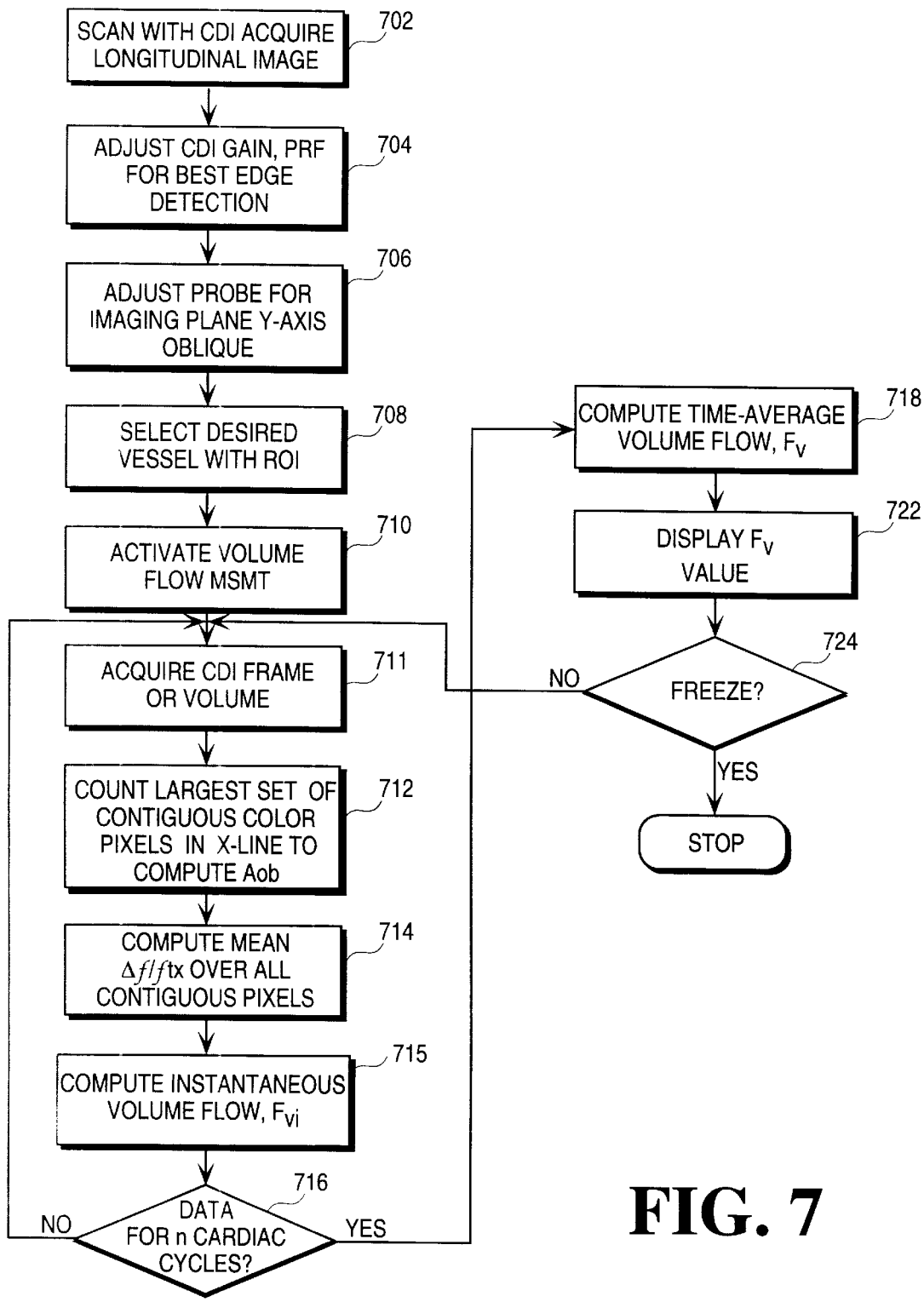
FIG. 7 is a flow chart illustrating the steps of measuring cross-sectional Doppler volume flow in a vessel, according to one embodiment of the present invention.

FIG. 7 is a flow chart illustrating the steps of measuring cross-sectional color Doppler volume flow in a vessel, according to one embodiment of the present invention. The method illustrated in FIG. 7 outlines the steps used to measure volume flow using a two-dimensional technique for calculating vessel cross-sectional area, as described in relation to FIGS. 3, 4A, and 4B. For purposes of explanation, the steps of the method illustrated in FIG. 7 will be discussed in reference to FIGS. 3, 4A, and 4B, however elements of the method of FIG. 7 are not limited to these specific embodiments.

In step 702 of FIG. 7, the vessel of interest is scanned using color Doppler imaging techniques. For the two-dimensional method of FIG. 3, CDI is used to scan a longitudinal section of the vessel. In step 704, the color gain, pulse repetition frequency (PRF), and filter thresholds are set to accurately display color up to the edge of blood flow or the luminal wall. Proper adjustment is important because under-colorization or over-colorization of the vessel lumen will result in underestimation or overestimation of the vessel cross-sectional area $A_{cs}$.

In step 706, the ultrasound transducer (probe) is positioned such that the y-axis defined by the imaging plane is oblique (≦68°) with respect to the direction of flow. For the two-dimensional method, the probe should be oriented and held relative to the vessel of interest as illustrated in FIGS. 3, 4A, and 4B. Once the probe is properly positioned, the CDI region-of-interest is positioned and sized to minimally enclose the vessel of interest, step 708. In step 710 the operator activates the cross-sectional color Doppler volume flow measurement.

Once activated by the operator, the color Doppler imaging apparatus (e.g., ultrasonic imaging system 100 in FIG. 2) is used to perform calculations to compute the Doppler flow measurement through the vessel. In step 711, a next CDI frame acquired. For the two-dimensional method, the number of colorized pixels is counted in the designated x-axis (x-axis 310 in FIG. 3), step 712. This number is used to compute the observed cross-sectional area $A_{ob}$. In step 714, the spatial-mean $\Delta f/f_{tx}$ is computed from all frequency shifts at each pixel identified in step 712. The value of $\Delta f/f_{tx}$ is then compared with that of previous CDI frames to locate the systolic peak. Each pair of successive systolic peaks identifies an integral cardiac cycle. In step 715, the instantaneous volume flow, $F_{vi}$, is computed.

In one embodiment of the present invention, steps 711 through 715 are repeated until a sufficient number of CDI frames have been acquired to provide data for a preset number, n, of complete cardiac cycles. For most applications n is an integer such as 1, 2, 3, and so on. In step 716 it is determined whether data for the desired number of cardiac cycles has been processed. If data for cardiac cycles is still to be acquired, the process repeats from step 711. If no further data is to be acquired, the process proceeds to step 718.

In step 718, the time-averaged volume flow, $F_v$, is computed. In step 722, the time-average cross-sectional color Doppler volume flow displayed (updated) on a display device, (e.g., video display 130 in FIG. 2).

In one embodiment of the present invention, this computation process is repeated with each successive set of CDI frames corresponding to the preset number (n), with continuous updating of the displayed value until the displayed image is frozen by the user. In step 724, it is determined whether the image display is frozen or stopped. If, in step 724, it is determined that the display process is not frozen, the process repeats from step 711, otherwise, the process stops and no further data acquisition is performed.

Figure 8:
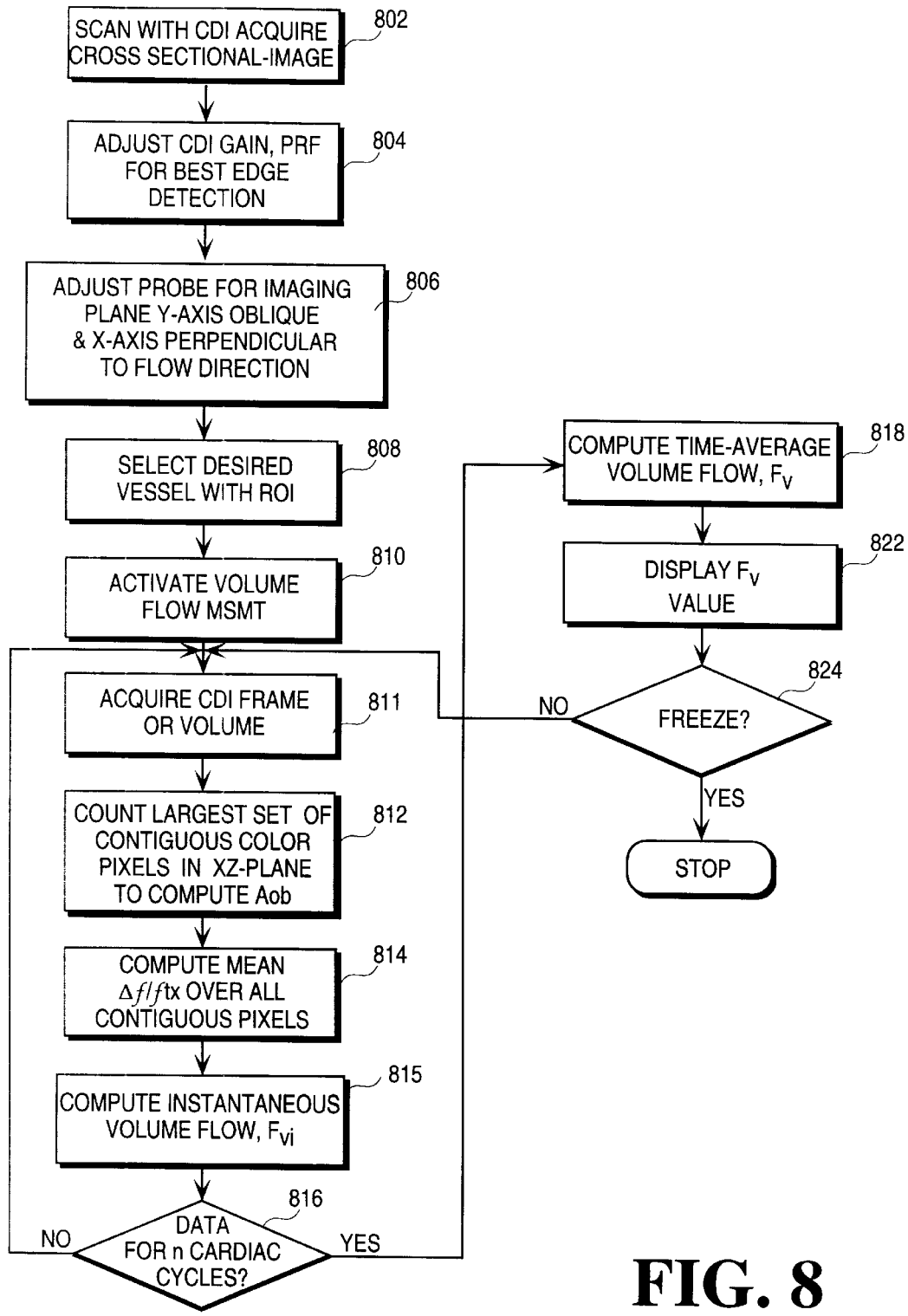
FIG. 8 is a flow chart illustrating the steps of measuring cross-sectional Doppler volume flow in a vessel, according to an alternative embodiment of the present invention.

FIG. 8 is a flow chart illustrating the steps of measuring cross-sectional color Doppler volume flow in vessel, according to an alternative embodiment of the present invention. The method illustrated in FIG. 8 outlines the steps used to measure volume flow using a three-dimensional technique for calculating vessel cross-sectional area, as described in relation to FIGS. 5, 6A, and 6B. For purposes of explanation, the steps of the method illustrated in FIG. 8 will be discussed in reference to FIGS. 5, 6A, and 6B, however elements of the method of FIG. 8 are not limited to these specific embodiments.

In step 802 of FIG. 8, the vessel of interest is scanned using color Doppler imaging techniques. For the three-dimensional method of FIG. 5, CDI is used to acquire a three-dimensional cross-sectional image of the vessel. In step 804, the color gain, PRF, and filter thresholds are set to accurately display color up to the edge of blood flow or the luminal wall. As stated earlier, proper adjustment is important because under-colorization or over-colorization of the vessel lumen will result in underestimation or overestimation of the vessel cross-sectional area $A_{cs}$.

In step 806, the ultrasound transducer (probe) is positioned such that the y-axis defined by the imaging plane is oblique (≦68°) with respect to the direction of flow. For three-dimensional imaging, the x-axis of the transducer must also be positioned approximately orthogonal to the direction of flow in the vessel, such that minimum lateral vessel diameter is displayed. For the three-dimensional method, the probe should be oriented and held relative to the vessel of interest as illustrated in FIGS. 5, 6A, and 6B. Once the probe is properly positioned, the CDI region-of-interest is positioned and sized to minimally enclose the vessel of interest, step 808. In step 810 the operator activates the cross-sectional Doppler volume flow measurement.

Once activated by the operator, the color Doppler imaging apparatus is used to perform calculations to compute the Doppler flow measurement through the vessel. In step 811, a next CDI frame acquired. For the three-dimensional method, the number of colorized pixels is counted in the largest set of contiguous pixels having the same flow direction within the designated transverse-plane region-of-interest (region 512 in FIG. 5), step 812. This number is used to compute the observed cross-sectional area $A_{ob}$. In step 814, the spatial-mean $\Delta f/f_{tx}$ is computed from all frequency shifts at each pixel identified in step 812. The value of $\Delta f/f_{tx}$ is then compared with that of previous CDI frames to locate the systolic peak. Each pair of successive systolic peaks identifies an integral cardiac cycle. In step 815, the instantaneous volume flow, $F_{vi}$ is computed.

In one embodiment of the present invention, steps 811 through 815 are repeated until a sufficient number of CDI frames have been acquired to provide data for a preset number, n, of complete cardiac cycles. In step 816 it is determined whether data for the desired number of cardiac cycles has been processed. If data for cardiac cycles is still to be acquired, the process repeats from step 811. If no further data is to be acquired, the process proceeds to step 818.

In step 818, the time-averaged volume flow, $F_v$, is computed. In step 822, the time-average cross-sectional color Doppler volume flow is displayed (updated) on a display device.

In one embodiment of the present invention, this computation process is repeated with each successive set of CDI frames corresponding to the preset number (n), with continuous updating of the displayed value until frozen or stopped by the operator. In step 824, it is determined whether the image display is frozen or stopped. If in step 824 it is determined that the display process is not frozen, the process repeats from step 811, otherwise, the process stops and no further data acquisition is performed.

Embodiments of the present invention provide Doppler flow measurement which is angle independent and provides a direct readout of velocity-based data. It is based on tracking vessel size and blood velocity at every sampling point in both a spatial (diameter or area) cross-section and in time. Thus, certain approximations or estimates that knowingly contribute to measurement error are eliminated. The main sources of error are not intrinsic to the technique, and can be minimized by careful scanning. Errors can be minimized by assuring lateral (x-axis) orthogonality to the direction of flow, and selecting an oblique imaging plane with $\theta \leq 68°$.

In the foregoing, a system has been described for measuring fluid flow in a vessel using color Doppler imaging techniques. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of measuring volume flow in a vessel using an ultrasonic imaging device, said method comprising the steps of:

positioning an ultrasonic transducer over the area of said vessel at an oblique angle relative to a vessel axis;

scanning a longitudinal area of a vessel using a color Doppler imaging method such that an imaging plane is formed approximately through the center of said vessel;

tabulating a number of color pixels along a line perpendicular to an axis of said transducer and spanning a height of said vessel and determining an observed cross-sectional area of said vessel using said number of color pixels;

spatially averaging a frequency shift of said number of color pixels;

computing a volume flow through said vessel from said observed cross-sectional diameter and said spatially averaged frequency shift said computing being independent of an angle of said transducer relative to said vessel; and time averaging said volume flow over one or more integral cardiac cycles.

2. The method of claim 1 further comprising the steps of:

defining a vessel axis within said longitudinal area of said vessel, said vessel axis corresponding to a direction of fluid flow through said vessel; and defining a cross-sectional axis that spans a cross-section of said imaging plane.

3. The method of claim 2 further comprising the step of positioning an ultrasound probe for performing said step of scanning said longitudinal area at an oblique Doppler angle relative to said vessel axis.

4. The method of claim 2 wherein said number of pixels comprise a plurality of contiguous color pixels representing uniform direction of flow through said vessel.

5. A method of measuring volume flow in a vessel using an ultrasonic imaging device, said method comprising the steps of:

positioning an ultrasonic transducer over the area of said vessel at an oblique angle relative to a vessel axis;

scanning a cross-sectional area of a vessel using a color Doppler imaging method to create a plurality of parallel image frames;

constructing a cross-sectional volume of said vessel by combining said plurality of parallel image frames;

tabulating a number of color pixels along a line perpendicular to an axis of said transducer and spanning a height of said vessel and determining an observed cross-sectional area of said vessel using said number of color pixels;

spatially averaging a frequency shift of said number of color pixels;

computing a volume flow through said vessel from said observed cross-sectional diameter and said spatially averaged frequency shift, said computing being independent of an angle of said transducer relative to said vessel; and time averaging said volume flow over one or more integral cardiac cycles.

6. The method of claim 5 further comprising the steps of:

defining a vessel axis within said cross-sectional area of said vessel, said vessel axis corresponding to a direction of fluid flow through said vessel;

defining an imaging axis corresponding to a linear plane of transmission of sound waves from an ultrasound probe used to perform said step of scanning said cross-sectional area; and defining a cross-sectional axis that spans a cross-section of said imaging plane.

7. The method of claim 6 further comprising the steps of:

positioning said ultrasound probe at an oblique Doppler angle relative to said vessel axis; and positioning said ultrasound probe such that said cross-sectional axis is approximately orthogonal to said vessel axis.

8. The method of claim 7 wherein said number of pixels comprise a plurality of contiguous color pixels representing uniform direction of flow through said vessel.

9. A method of performing ultrasonic imaging comprising the steps of:

defining a vessel axis corresponding to a direction of fluid flow through a vessel to be scanned using an ultrasonic imaging device;

positioning an ultrasound probe relative to said vessel such that sound waves transmitted by said ultrasound probe are incident to said vessel axis at an oblique angle;

activating a cross-sectional color Doppler volume flow measurement in an area of said vessel;

tabulating a number of color pixels along a line perpendicular to an axis of said probe and spanning a height of said vessel;

determining an observed cross-sectional area of said vessel using said number of color pixels;

calculating a volume flow through said vessel from said observed cross-sectional area and frequency shift information for each pixel of said number of color pixels, said calculating being independent of an angle of said probe relative to said vessel; and time averaging said volume flow over one or more integral cardiac cycles.

10. The method of claim 9 further comprising the step of positioning said ultrasound probe such that a linear transmission plane of said ultrasound probe is longitudinally aligned with said vessel axis.

11. The method of claim 10 wherein said oblique angle is an angle that is less than 68 degrees.

12. The method of claim 11 further comprising the steps of:

acquiring color Doppler imaging values for fluid flow through said area of said vessel for a plurality of color Doppler imaging frames;

computing a spatial mean frequency shift for said each pixel of said number of pixels for each frame of said plurality of color Doppler imaging frames;

computing a volume flow for each observed cross-sectional area using each imaging frame of said plurality of color Doppler imaging frames; and computing a time-averaged volume flow through said vessel.

13. The method of claim 12 further comprising the steps of:

scan converting said Doppler imaging values for complete frames of said plurality of color Doppler imaging frames into a raster format; and assigning color values to said Doppler imaging values for display on a display device.

14. The method of claim 13 wherein said plurality of frames are collected for one or more cardiac cycles.

15. The method of claim 9 wherein said time-averaged volume flow is displayed numerically on a display device and updated at the completion of each successive cardiac cycle of said one or more integral cardiac cycles.

16. A method of performing ultrasonic imaging comprising the steps of:

defining a vessel axis corresponding to a direction of fluid flow through a vessel to be scanned using an ultrasonic imaging device;

positioning an ultrasound probe relative to said vessel such that sound waves transmitted by said ultrasound probe are incident to said vessel axis at an oblique angle, and such that the linear transmission plane of said ultrasound probe is approximately orthogonal to said vessel axis;

activating a cross-sectional color Doppler volume flow measurement in an area of said vessel;

tabulating a number of color pixels in an oblique plane region defined by said sound waves incident in said area of said vessel and along a line perpendicular to an axis of said probe;

determining an observed cross-sectional area of said vessel using said number of color pixels;

calculating a volume flow through said vessel from said observed cross-sectional area and frequency shift information for each pixel of said number of color pixels, said calculating being independent of an angle of said probe relative to said vessel; and time averaging said volume flow over one or more integral cardiac cycles.

17. The method of claim 16 further comprising the step of positioning said ultrasound probe such that the displayed lateral vessel diameter is minimized.

18. The method of claim 17 wherein said oblique angle is an angle that is less than 68 degrees.

19. The method of claim 18 further comprising the steps of:

acquiring color Doppler imaging values for fluid flow through said area of said vessel for a plurality of color Doppler imaging frames;

computing a spatial mean frequency shift for said each pixel of said number of pixels for each frame of said plurality of color Doppler imaging frames;

computing a volume flow for each observed cross-sectional area using each imaging frame of said plurality of color Doppler imaging frames; and computing a time-averaged volume flow through said vessel.

20. The method of claim 19 further comprising the steps of:

scan converting said Doppler imaging values for complete frames of said plurality of color Doppler imaging frames into a raster format; and assigning color values to said Doppler imaging values for display on a display device.

21. The method of claim 20 wherein said plurality of frames are collected for one or more cardiac cycles.

22. The method of claim 16 wherein said time-averaged volume flow is displayed numerically on a display device and updated at the completion of each successive cardiac cycle of said one or more integral cardiac cycles.

* * * * *

UNITED STATES PATENT AND TRADEMARK OFFICE
CERTIFICATE OF CORRECTION

PATENT NO. : 6,071,242
DATED : June 6, 2000
INVENTOR(S) : Lin

It is certified that error appears in the above-identified patent and that said Letters Patent is hereby corrected as shown below:

In column 7 at line 31, delete "$\overline{A + scob}$" and insert -- $\overline{Aob}$ --.

Signed and Sealed this

Third Day of April, 2001

Attest:

NICHOLAS P. GODICI

*Attesting Officer*     *Acting Director of the United States Patent and Trademark Office*